US00PP33726P2

(12) United States Plant Patent
Pounders

(10) Patent No.: US PP33,726 P2
(45) Date of Patent: Dec. 7, 2021

(54) ***LAGERSTROEMIA* PLANT NAMED 'JBG 19101'**

(50) Latin Name: ***Lagerstroemia* hybrid**
Varietal Denomination: JBG 19101

(71) Applicant: Capstone Plants, Inc., Grand Saline, TX (US)

(72) Inventor: Cecil Pounders, Decatur, AL (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 17/231,251

(22) Filed: Apr. 15, 2021

(51) Int. Cl.
*A01H 5/00* (2018.01)

(52) U.S. Cl.
USPC ..... Plt./252

(58) Field of Classification Search
USPC ..... Plt./252
See application file for complete search history.

*Primary Examiner* — Annette H Para
(74) *Attorney, Agent, or Firm* — The Webb Law Firm

(57) ABSTRACT

A new and distinct *Lagerstroemia* plant having red colored flowers with dark colored foliage and a large growth habit.

4 Drawing Sheets

Botanical classification: *Lagerstroemia* hybrid.
Varietal denomination: 'JBG 19101'.

BACKGROUND OF THE INVENTION

The present invention comprises a new and distinct *Lagerstroemia* hybrid plant having the varietal name 'JBG 19101'. The new variety is the result of a planned breeding program with the purposes of developing *Lagerstroemia* plants with intense colored foliage and large, dark colored flowers with an upright growth habit. 'JBG 19101' is the result of a cross conducted in Decatur, Ala. between a *L. indica* x *L. limii* variety referred to as 'IP-LIL-79' (female parent, unpatented) and the unnamed result of a cross between *L. indica* varieties named 'Embers' and 'Ebony Fire' (both believed unpatented) as the male parent. The new variety was selected in 2017 in Decatur, Ala. and the first asexual reproduction of the new variety was conducted by vegetative cuttings in July of 2017 in Decatur, Ala. 'JBG 19101' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 19101' is similar to its female parent in vigor, but its female parent exhibits green foliage and pink colored flowers. Similar to its male parent, 'JBG 19101' has dark colored foliage and red colored flowers. However, 'JBG 19101' is more vigorous in growth than its male parent and exhibits an improved foliage texture.

When 'JBG 19101' is compared to *L. indica* variety 'Tuscarora' (believed unpatented), both varieties exhibit vigorous plant growth and development, improved *Cercospora* leaf spot and powdery mildew resistance, and long flowering cycles (from spring through fall). However, 'JBG 19101' exhibits dark colored foliage that maintains consistent coloring through fall, while 'Tuscarora' exhibits green colored foliage that becomes orange-red in color in the fall. Further, 'JBG 19101' has red colored flowers, while 'Tuscarora' has dark pink colored flowers.

The following traits distinguish 'JBG 19101' as a new and distinct cultivar from other *Lagerstroemia* varieties known to the breeder:

1. Primarily vase-shaped and large growth habit;
2. More upright and better branching;
3. Large and flat leaves; and
4. Improved *Cercospora* leaf spot and powdery mildew resistance.

DESCRIPTION OF THE DRAWINGS

The accompanying photographic images illustrate the new variety, with the colors being as nearly true as is possible with color illustrations of this type.

DESCRIPTION OF THE PLANT

Figure 1:
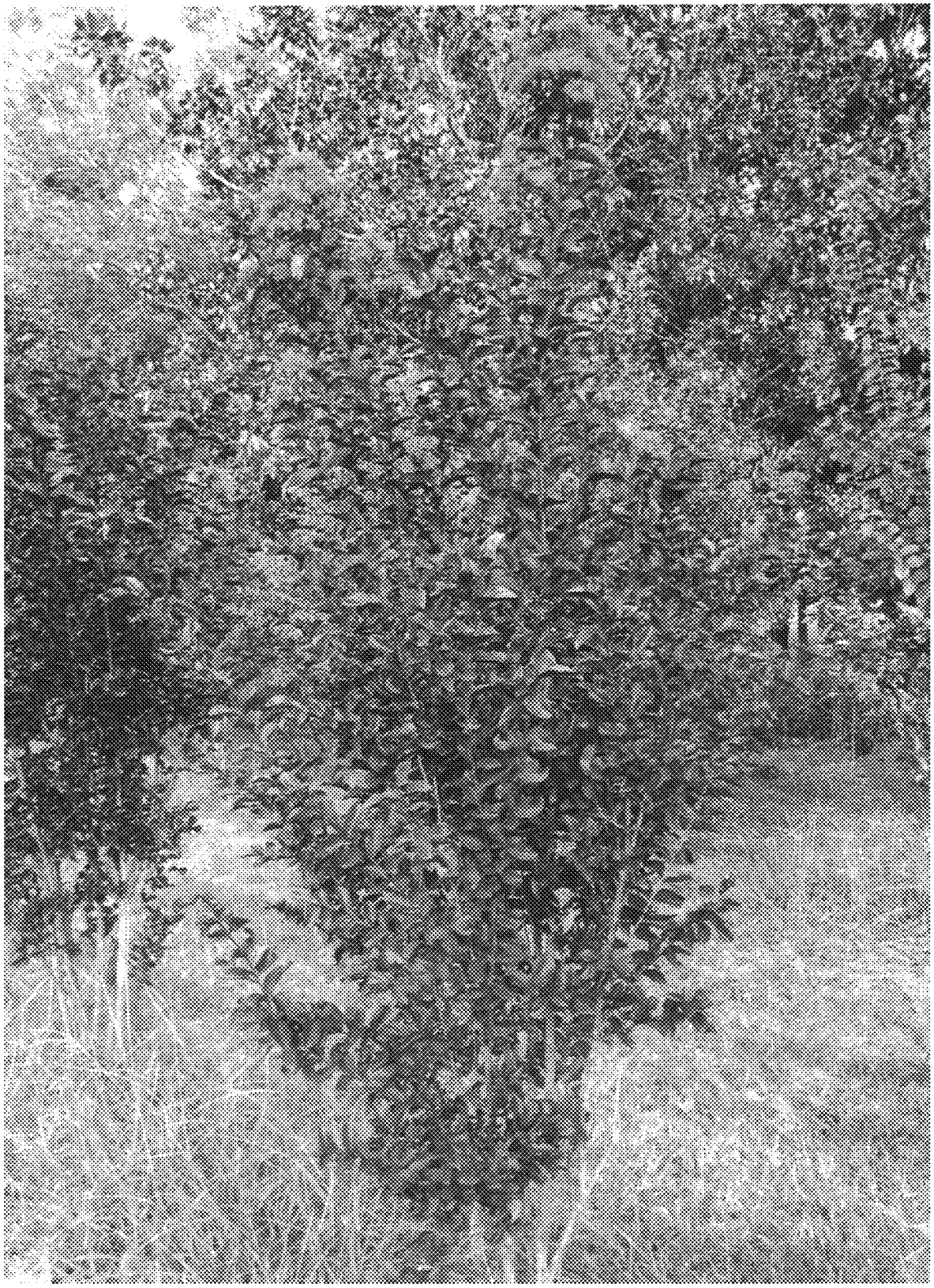
FIG. 1 illustrates a flowering plant of the new variety at approximately 5 years of age.
Figure 2:
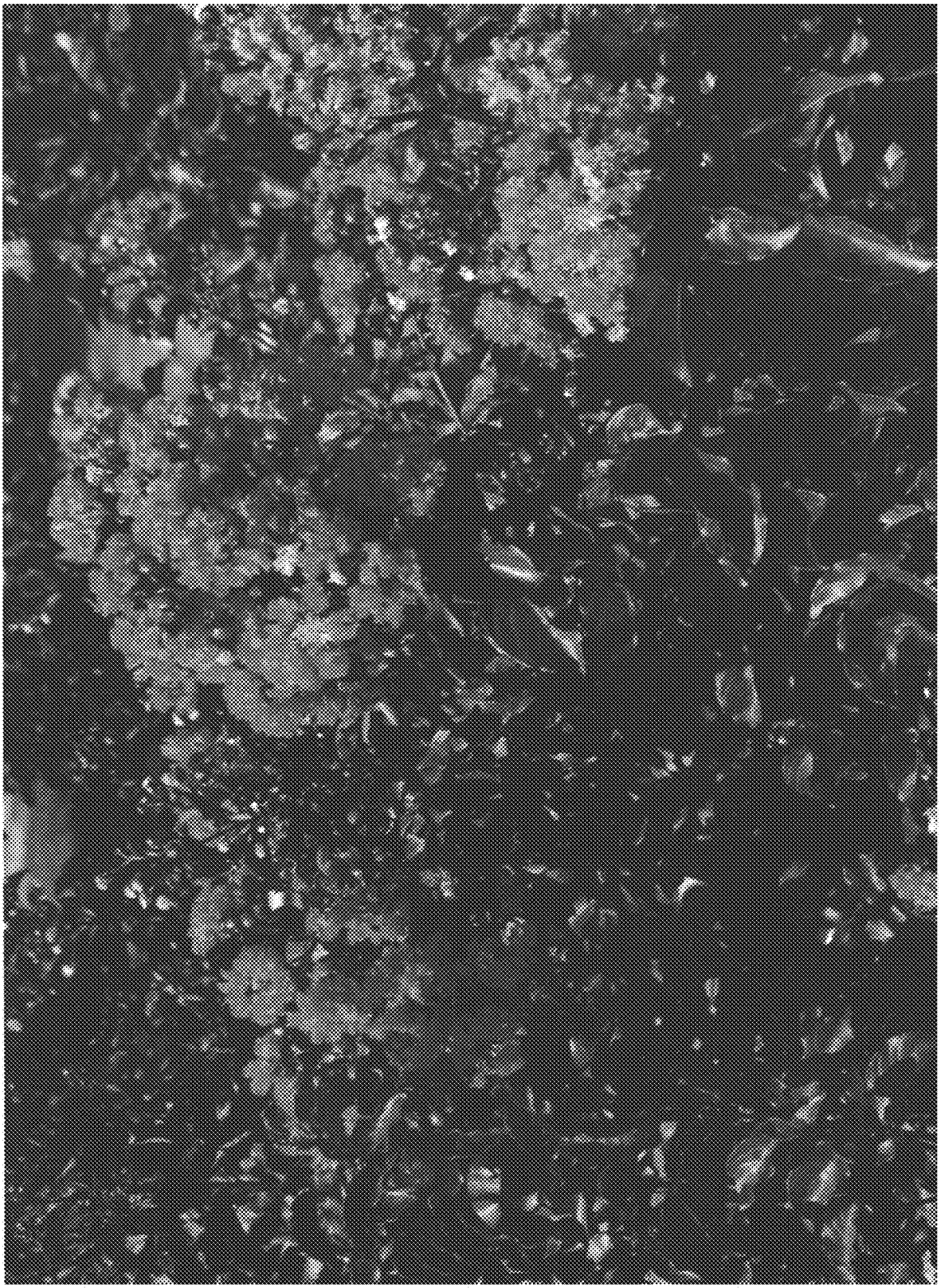
FIG. 2 illustrates flowering plants of the new variety at approximately 1 year of age.
Figure 3:
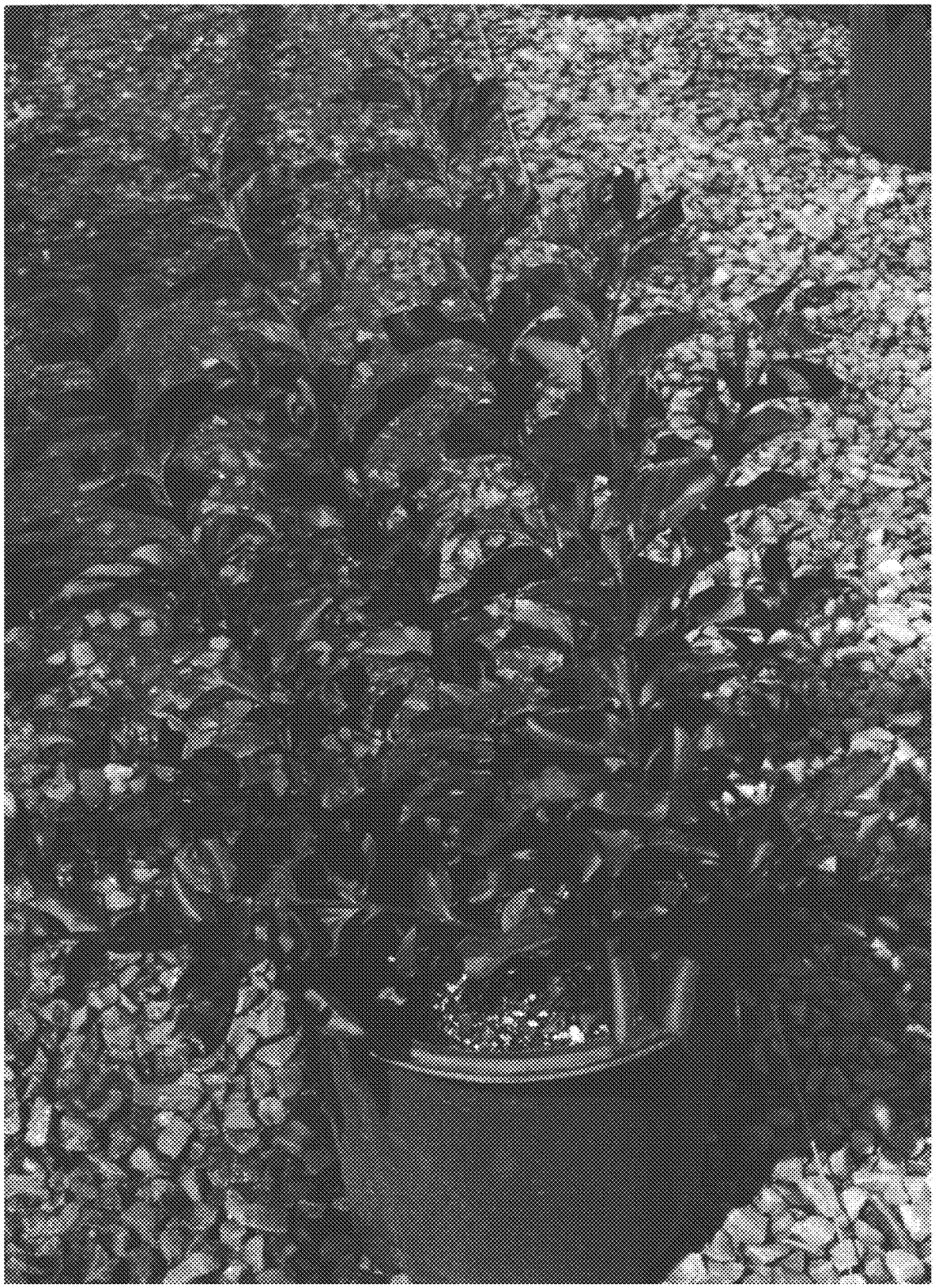
FIG. 3 illustrates a young plant of the new variety at approximately 2 months of age.
Figure 4:
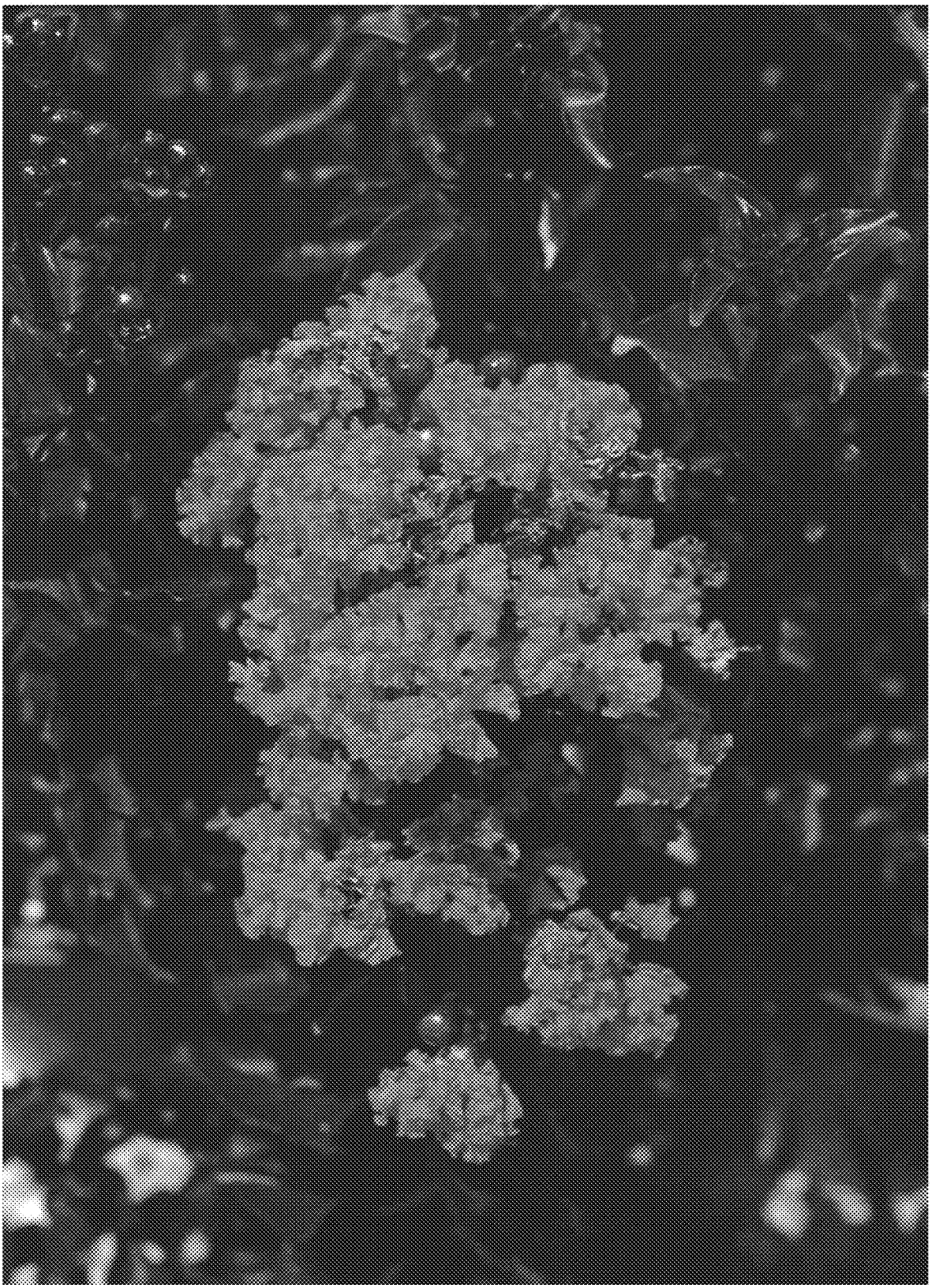
FIG. 4 illustrates a close-up view of a flowering plant of the new variety at approximately 1 year of age.

The following detailed description sets forth the characteristics of the new variety at approximately 10 months of age. The plants were grown in 2 gallon containers in organic, artificial soil with a 9 month slow release fertilizer and overhead irrigation as needed. The color readings and measurements were taken indoors in Grand Saline, Tex. under fluorescent lighting and near the natural light of a window. Color references are primarily to The 1995 R.H.S. Colour Chart of The Royal Horticultural Society of London, 3$^{rd}$ Edition, except where general color terms are used.

PLANT

Time to initiate roots: About 10 days at an average of 26° C.
Time to develop roots: About 15 days at an average of 26° C.

Time to beginning of flowering: About 45 days at an average of 26° C.
Root description: Medium coarse, non-fibrous, and non-tap roots.
Growth habit: Upright.
Form: V-shaped, upright with vertical branching, taller than wide, narrowing upward spread.
Height: Approximately 1.0 m from the base of the pot to the top of the plant.
Diameter: Approximately 0.5 in at the widest part of the plant.
Vigor: High.
Specific disease/pest resistance: improved leaf spot (*Cercospora lythracearum* and *Xanthomonas* sp.) and powdery mildew (*Erysiphe* sp.) resistance.
Heat/cold tolerance: USDA Zone 6.
Drought tolerance: Observed.
Lasting quality: Under proper care, the new variety could last over a century.
Main stem/trunk:
*Height*.—Approximately 0.8 m.
*Diameter*.—Approximately 1.3 cm.
*Color*.—200D.
*Texture*.—Smooth, with faintly textured.
*Pubescence*.—None present.
*Form*.—Erect.
Branching habit: Vertical with narrow angles.
Lateral branches:
*Length*.—From 0.3 m to 0.6 m.
*Diameter*.—From 0.6 cm to 1.0 cm, sometimes smaller.
*Internode length*.—From 3.2 cm to 14.0 cm.
*Texture*.—Smooth, with fewer lines than the trunk.
*Pubescence*.—None present.
*Color*.—Older branches are 200C, newer branches are 187B.

FOLIAGE

Leaves:
*Arrangement*.—Alternate.
*Size*.—Length: From 6.0 to 7.6 cm. Width: From 3.8 to 4.4 cm.
*Shape*.—Elliptical to ovate.
*Apex*.—Acute for younger leaves, apiculate for older leaves.
*Base*.—Gradually tapering/obtuse.
*Texture*.—Upper surface: Smooth. Lower surface: Slightly textured.
*Margin*.—Entire.
*Pubescence*.—None present.
*Color*.—Young leaves: Upper surface: 183B. Lower surface: 183C. Mature leaves: Upper surface: 200A. Lower surface: 200B.
Petiole:
*Shape*.—Round.
*Length*.—Approximately 1.6 mm.
*Diameter*.—Approximately 1.6 mm.
*Color*.—178A.
Pedicel:
*Length*.—Approximately 0.8 cm.
*Width*.—Approximately 1.6 mm.
*Color*.—63A.
Stipule:
*Shape*.—Seal like.
*Length*.—4.0 mm.
*Diameter*.—2.0 mm.
Veins:
*Type*.—Pinnate, but veins do not always line up in the center.
*Color*.—Upper surface: 187A. Lower surface: 184A.
Bracts: Fused.

FLOWERS

Bud:
*Shape*.—Rounded and tapered.
*Diameter*.—8.0 mm.
*Length*.—7.0 mm.
*Color*.—187B.
Flowering season: From mid-June to Mid-October in Grand Saline, Tex. and Decatur, Ala.
Flower:
*Form*.—Panicle clusters.
*Type*.—Rotate.
*Diameter*.—Approximately 3.8 cm.
*Arrangement*.—The petals extend from a star-shaped base with 6 points.
*Lastingness*.—2-3 days per flower.
*Fragrance*.—Slightly sweet.
Spike:
*Number of flowers per spike*.—From 30-55.
*Length*.—Approximately 9.0 to 17.0 cm.
*Diameter*.—Approximately 4.5 to 14.5 cm.
Corolla:
*Form*.—Actinomorphic.
*Petals*.—Number: 6. Length: 14.0 mm. Width: 12.0 mm. Shape: Curved, with taller edges and a shallow center. Color: Upper surface: 53C. Lower surface: 53D.
Sepals:
*Form*.—6-fused.
*Length*.—6.0 mm.
*Diameter*.—4.0 mm.
*Shape*.—Each sepal s triangular and the fused sepals form a star shape.
*Apex*.—Rounded.

REPRODUCTIVE ORGANS

Stamens:
*Number*.—7 per flower.
*Length*.—22.0 mm.
*Filament length*.—20.0 mm.
*Filament color*.—51A.
*Anthers*.—Shape: Long and oval. Length: 2.0 mm. Color: 51A.
*Pollen*.—Amount: From 30/35 to prolific count. Color: 13B.
Pistils:
*Number*.—1.
*Length*.—13.0 mm.
*Style*.—Length: 12.0 mm. Color: 56D.
*Stigma*.—Shape: Walnut. Color: 166C. Ovary color: 153D.

SEEDS

Seeds:
*Production conditions*.—Long, sunny days at temperatures of 29-38° C.
*Size*.—9.0 cm in diameter.
*Color*.—144A at the lower part, fading to 187B at the top.

I claim:

1. A new and distinct variety of *Lagerstroemia* plant, as is herein illustrated and described.

* * * * *